(12) United States Patent
Gross

(10) Patent No.: US 11,877,863 B2
(45) Date of Patent: Jan. 23, 2024

(54) APPARATUS, SYSTEMS, AND METHODS FOR MONITORING RESPIRATORY FUNCTION

(71) Applicant: Michael Gross, Halifax (CA)

(72) Inventor: Michael Gross, Halifax (CA)

(73) Assignee: InkWell Health Ltd., Burlington (CA)

( * ) Notice: Subject to any disclaimer, the term of this patent is extended or adjusted under 35 U.S.C. 154(b) by 470 days.

(21) Appl. No.: 17/215,137

(22) Filed: Mar. 29, 2021

(65) Prior Publication Data

US 2021/0298673 A1 Sep. 30, 2021

Related U.S. Application Data

(60) Provisional application No. 63/000,708, filed on Mar. 27, 2020.

(51) Int. Cl.
| | |
|---|---|
| *A61B 5/01* | (2006.01) |
| *A61B 5/00* | (2006.01) |
| *A61B 5/08* | (2006.01) |
| *A61B 5/11* | (2006.01) |
| *G06T 7/00* | (2017.01) |

(52) U.S. Cl.
CPC .......... *A61B 5/6804* (2013.01); *A61B 5/0008* (2013.01); *A61B 5/0013* (2013.01); *A61B 5/0022* (2013.01); *A61B 5/0077* (2013.01); *A61B 5/01* (2013.01); *A61B 5/08* (2013.01); *A61B 5/6814* (2013.01); *A61B 5/6832* (2013.01); *A61B 5/6898* (2013.01); *A61B 5/1128* (2013.01); *G06T 7/0016* (2013.01)

(58) Field of Classification Search
CPC ... A61B 5/6804; A61B 5/0008; A61B 5/0013; A61B 5/0022; A61B 5/0077; A61B 5/01; A61B 5/08; A61B 5/6814; A61B 5/6832; A61B 5/6898; A61B 5/1128; A61B 5/0806; A61B 5/0816; A61B 5/1127; A61B 5/1135; A61B 2505/07; A61B 5/0002; G06T 7/0016
USPC ........................................................ 382/128
See application file for complete search history.

(56) References Cited

U.S. PATENT DOCUMENTS

| | | | |
|---|---|---|---|
| 7,878,979 B2* | 2/2011 | Derchak | A61B 5/1135 600/534 |
| 2019/0080803 A1* | 3/2019 | Lotan | G16H 50/30 |

\* cited by examiner

*Primary Examiner* — Charlotte M Baker
(74) *Attorney, Agent, or Firm* — Bereskin & Parr LLP

(57) ABSTRACT

Systems for monitoring respiratory function of a person include a garment configured to be worn on a torso of the person. The garment includes one or more reference patterns positioned on the anterior torso of the person when the garment is worn. A camera is used to capture, at a first time, at least one image of the person immediately prior to inhalation, and immediately prior to exhalation, and to capture, at a second time, at least one image of the person immediately prior to inhalation, and immediately prior to exhalation. A computing device is used to transmit the images to a remote computing device for analysis.

20 Claims, 6 Drawing Sheets

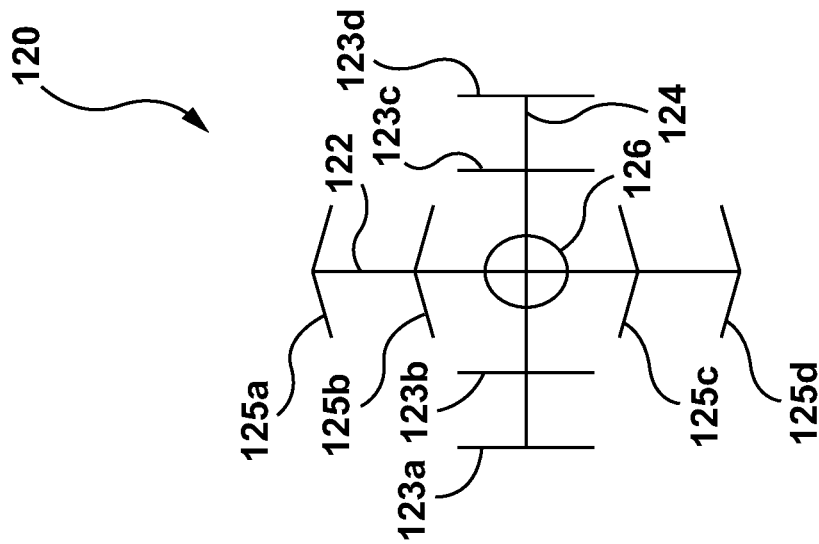
FIG. 3c
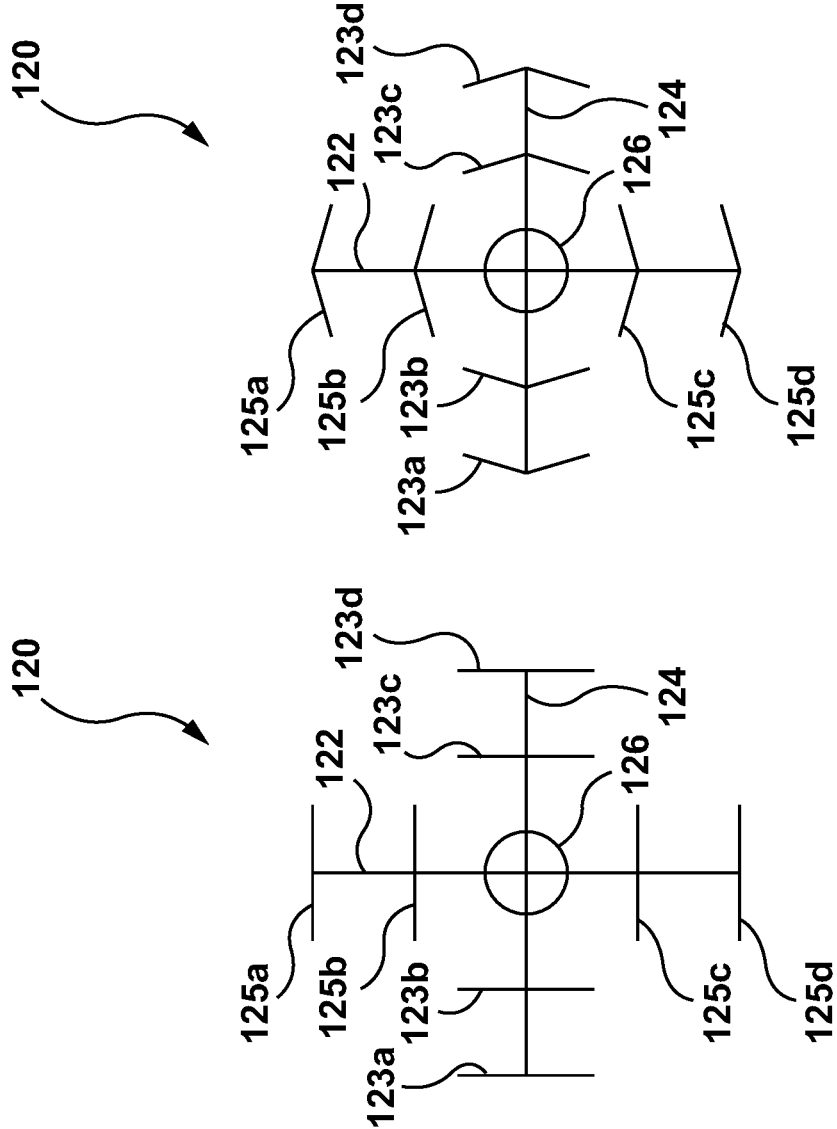
FIG. 3b
FIG. 3a

APPARATUS, SYSTEMS, AND METHODS FOR MONITORING RESPIRATORY FUNCTION

CROSS-REFERENCE

This application claims the benefit of U.S. Provisional Patent Application No. 63/000,708 filed Mar. 27, 2020, which is hereby incorporated herein by reference.

FIELD

This disclosure relates generally to apparatus, systems, and methods for monitoring respiratory function, and more specifically to apparatus, systems, and methods that allow for remote (e.g. in-home) monitoring of respiratory function, e.g. as an adjunct to out-patient monitoring of persons with respiratory compromise.

INTRODUCTION

Persons with diagnosed or suspected health conditions that typically impact respiratory function may benefit from periodic or continuous monitoring of their respiratory function. Such monitoring may assist in diagnosing the severity and/or the existence of a health condition.

Typically, respiratory function is monitored by a health care professional, often in a hospital or clinic setting.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In some situations, it may be desirable to monitor the respiratory function of a person remotely, e.g. with the patient in a location remote from a hospital, clinic, or other healthcare facility (e.g. in the person's home).

For example, it may be desirable to monitor the respiratory function of a person of a person who has been assessed in a clinical, hospital, or emergency room setting and was sent home as they were not sick enough to admit at the time they were assessed. Such persons have been characterized as falling within a "Discharge Gap".

It may also be desirable to monitor the respiratory function of a person without that person directly interacting with a healthcare professional, e.g. via a 'house call'.

The apparatus, systems, and methods disclosed herein may facilitate the monitoring of a person's respiratory function without requiring direct interaction with a healthcare professional. For example, in a preferred embodiment, a smartphone (or other computing device) may be used to record images of a person breathing while wearing a garment on their torso, the garment having one or more reference patterns positioned over the person's lungs (e.g. at approximately nipple-level for males, or at approximately mid-to upper breast level in females). The one or more reference patterns provide visual landmarks that may be used to estimate one or more aspects of respiratory function (e.g. chest expansion), e.g. by comparing images taken of the person's torso at different points in a respiratory cycle.

In accordance with one broad aspect of this disclosure, there is provided a system for monitoring respiratory function of a person, the system comprising: a garment configured to be worn on a torso of the person, the garment comprising a first reference pattern positioned to overlie a first lung of the person when the garment is worn, and a second reference pattern positioned to overlie a second lung of the person when the garment is worn; a camera configured to capture, at a first time, at least one image of the person immediately prior to inhalation, and at least one image of the person immediately prior to exhalation, and configured to capture, at a second time, at least one image of the person immediately prior to inhalation, and at least one image of the person immediately prior to exhalation; and a computing device comprising a processor and a memory, the processor configured to execute instructions of one or more application modules, the execution of the one or more application modules causing the processor to: establish a communication channel between the computing device and a remote computing device; transmit, to the remote computing device, the at least one image of the person immediately prior to inhalation, and the at least one image of the person immediately prior to exhalation, captured at the first time; and transmit, to the remote computing device, the at least one image of the person immediately prior to inhalation, and the at least one image of the person immediately prior to exhalation, captured at the second time.

In some embodiments, the computing device comprises the camera.

In some embodiments, the computing device is a mobile computing device.

In some embodiments, the computing device is a smartphone.

In some embodiments, the first reference pattern and the second reference pattern are vertically aligned with each other when the garment is worn and the torso of the person is generally upright.

In some embodiments, the camera is configured to capture the at least one image of the person immediately prior to inhalation, and the at least one image of the person immediately prior to exhalation, taken at the first time, as a video clip of a breathing cycle of the person.

In some embodiments, the execution of the one or more application modules further cause the processor to: determine a measure of respiratory function for the person at the first time, based on a comparison of: a relative size, shape, and/or position of the first and second reference patterns in the at least one image of the person immediately prior to inhalation, captured at the first time; and a relative size, shape, and/or position of the first and second reference patterns in the at least one image of the person immediately prior to exhalation, captured at the first time.

In some embodiments, the execution of the one or more application modules further cause the processor to: determine a measure of respiratory function for the person at the second time, based on a comparison of: a relative size, shape, and/or position of the first and second reference patterns in the at least one image of the person immediately prior to inhalation, captured at the second time; and a relative size, shape, and/or position of the first and second reference patterns in the at least one image of the person immediately prior to exhalation, captured at the second time.

In some embodiments, the execution of the one or more application modules further cause the processor to: determine a relative measure of respiratory function for the person, based on the determined measure of respiratory function for the person at the first time and the determined measure of respiratory function for the person at the second time.

In some embodiments, the garment further comprises a third reference pattern positioned inferior of a sternum of the person when the garment is worn.

In some embodiments, the execution of the one or more application modules further cause the processor to: determine a measure of respiratory function for the person at the first time, based on a comparison of: a relative size, shape, and/or position of at least two of the first, second, and third reference patterns in the at least one image of the person immediately prior to inhalation, captured at the first time; and a relative size, shape, and/or position of at least two of the first, second, and third reference patterns in the at least one image of the person immediately prior to exhalation, captured at the first time.

In some embodiments, the execution of the one or more application modules further cause the processor to: determine a measure of respiratory function for the person at the second time, based on a comparison of: a relative size, shape, and/or position of at least two of the first, second, and third reference patterns in the at least one image of the person immediately prior to inhalation, captured at the second time; and a relative size, shape, and/or position of at least two of the first, second, and third reference patterns in the at least one image of the person immediately prior to exhalation, captured at the second time.

In some embodiments, the execution of the one or more application modules further cause the processor to: determine a relative measure of respiratory function for the person, based on the determined measure of respiratory function for the person at the first time and the determined measure of respiratory function for the person at the second time.

In some embodiments, the system further comprises: a sensor configured to be adhered to a forehead of the person, the sensor configured to provide a visual indication of a temperature of the person; wherein the camera is further configured to capture at least one image of the sensor when adhered to the forehead of the person; and wherein the execution of the one or more application modules further cause the processor to: transmit, to the remote computing device, the at least one image of the sensor.

In accordance with one broad aspect of this disclosure, there is provided a method for monitoring respiratory function of a person, the method comprising: providing a garment configured to be worn on a torso of the person, the garment comprising a first reference pattern positioned to overlie a first lung of the person when the garment is worn, and a second reference pattern positioned to overlie a second lung of the person when the garment is worn; at a first time, capturing, using a camera, at least one image of the person immediately prior to inhalation, and at least one image of the person immediately prior to exhalation, at a second time, capturing, using the camera, at least one image of the person immediately prior to inhalation, and at least one image of the person immediately prior to exhalation; transmitting, to a remote location, the at least one image of the person immediately prior to inhalation, and the at least one image of the person immediately prior to exhalation, captured at the first time; and transmitting, to the remote location, the at least one image of the person immediately prior to inhalation, and the at least one image of the person immediately prior to exhalation, captured at the second time.

In some embodiments, the capturing and the transmitting are performed using a mobile computing device comprising the camera, a processor, and a memory.

In some embodiments, the mobile computing device is a smartphone.

In some embodiments, the method further comprises: determining a measure of respiratory function for the person at the first time, based on a comparison of: a relative size, shape, and/or position of the first and second reference patterns in the at least one image of the person immediately prior to inhalation, captured at the first time; and a relative size, shape, and/or position of the first and second reference patterns in the at least one image of the person immediately prior to exhalation, captured at the first time.

In some embodiments, the method further comprises: determining a measure of respiratory function for the person at the second time, based on a comparison of: a relative size, shape, and/or position of at least two of the first, second, and third reference patterns in the at least one image of the person immediately prior to inhalation, captured at the second time; and a relative size, shape, and/or position of at least two of the first, second, and third reference patterns in the at least one image of the person immediately prior to exhalation, captured at the second time.

In some embodiments, the method further comprises: determining a relative measure of respiratory function for the person, based on the determined measure of respiratory function for the person at the first time and the determined measure of respiratory function for the person at the second time.

It will be appreciated by a person skilled in the art that a method or apparatus disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIG. 3A is a reference pattern in accordance with another embodiment, in a neutral configuration;

FIG. 3B is the reference pattern of FIG. 3A in a first stretched configuration;

FIG. 3C is the reference pattern of FIG. 3A in a second stretched configuration;

Figure 1:
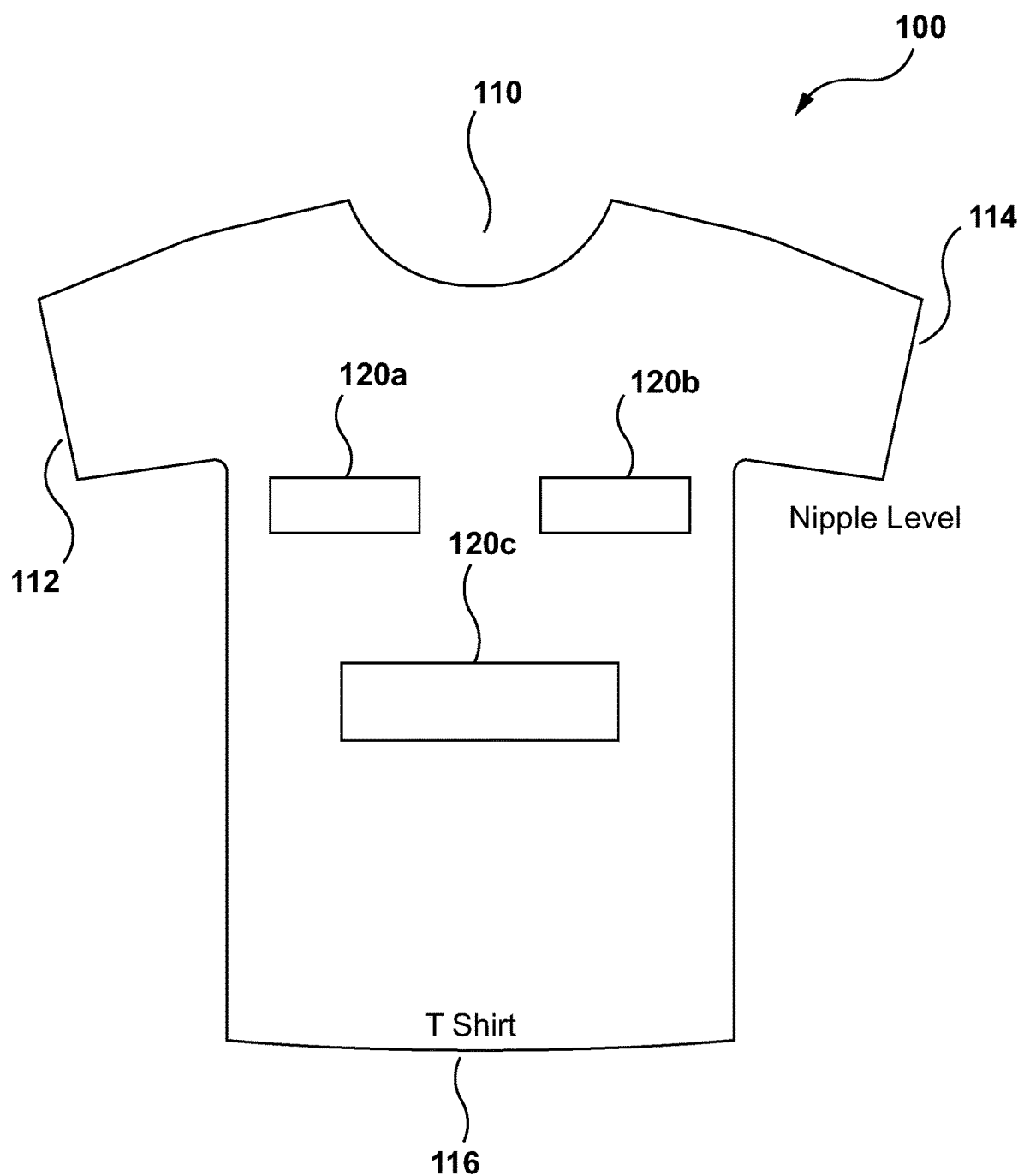
FIG. 1 is a front view of a garment with reference patterns on the anterior torso portion in accordance with one embodiment.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The apparatus, systems, and methods disclosed herein are described specifically in relation to collecting and transmitting images and/or other data to one or more medical professionals. Based on the data, the medical professional(s) can assess, diagnose, recommend, and/or provide medical treatment, and/or communicate with the person as necessary.

For example, embodiments described herein may allow a person to use their smartphone (or other computing device) to capture images and/or video of themselves while breathing using a camera of the smartphone (or other computing device) while they are wearing a provided garment. The person can use their smartphone (or other computing device) to send the captured images and/or video to a remote computing device for storage, analysis, and/or for redistribution to a physician for assessment.

Advantageously, the apparatus, systems, and methods disclosed herein may be used on an out-patient basis, to monitor changes over time, such that a deteriorating condition may be identified by a medical practitioner earlier than would normally be expected from monitoring by the patient or non-skilled care giver.

Additionally, the apparatus, systems, and methods disclosed may allow medical professionals (e.g. physicians, surgeons, nurses, etc.) to measure and monitor respiratory function of a patient (or prospective patient) without having to physically see them in person. This may be considered advantageous if the patient has been diagnosed with (or is exhibiting symptoms of) a highly communicable disease or infection.

FIG. 1 illustrates an example embodiment of a garment that can be worn on a person's torso, in this example a T-shirt, referred to generally as 100. With reference to FIG. 1, garment 100 includes a neck opening 110, arm openings 112, 114, and a waist opening 116.

Garment 100 also includes reference patterns on the anterior torso portion 118 of the garment. In the illustrated example, a first reference pattern 120*a* is positioned such that it overlies a first lung of the person when the garment is worn, and a second reference pattern 120*b* is positioned such that it overlies a first lung of the person when the garment is worn. Providing reference patterns on each side of the torso may have one or more advantages. For example, such an arrangement may facilitate measurement of asymmetric chest expansion.

Garment 100 also includes a third reference pattern 120*c* positioned to be inferior of a sternum of the person when the garment is worn. Providing a reference pattern at such a location may facilitate a measurement of diaphragmatic breathing, where the stomach tends to move more, although body habitus may make it difficult to obtain an accurate assessment.

While three reference patterns are illustrated in the example of FIG. 1, it will be appreciated that two, one, or four or more reference patterns may be provided in alternative embodiments.

Figure 2:
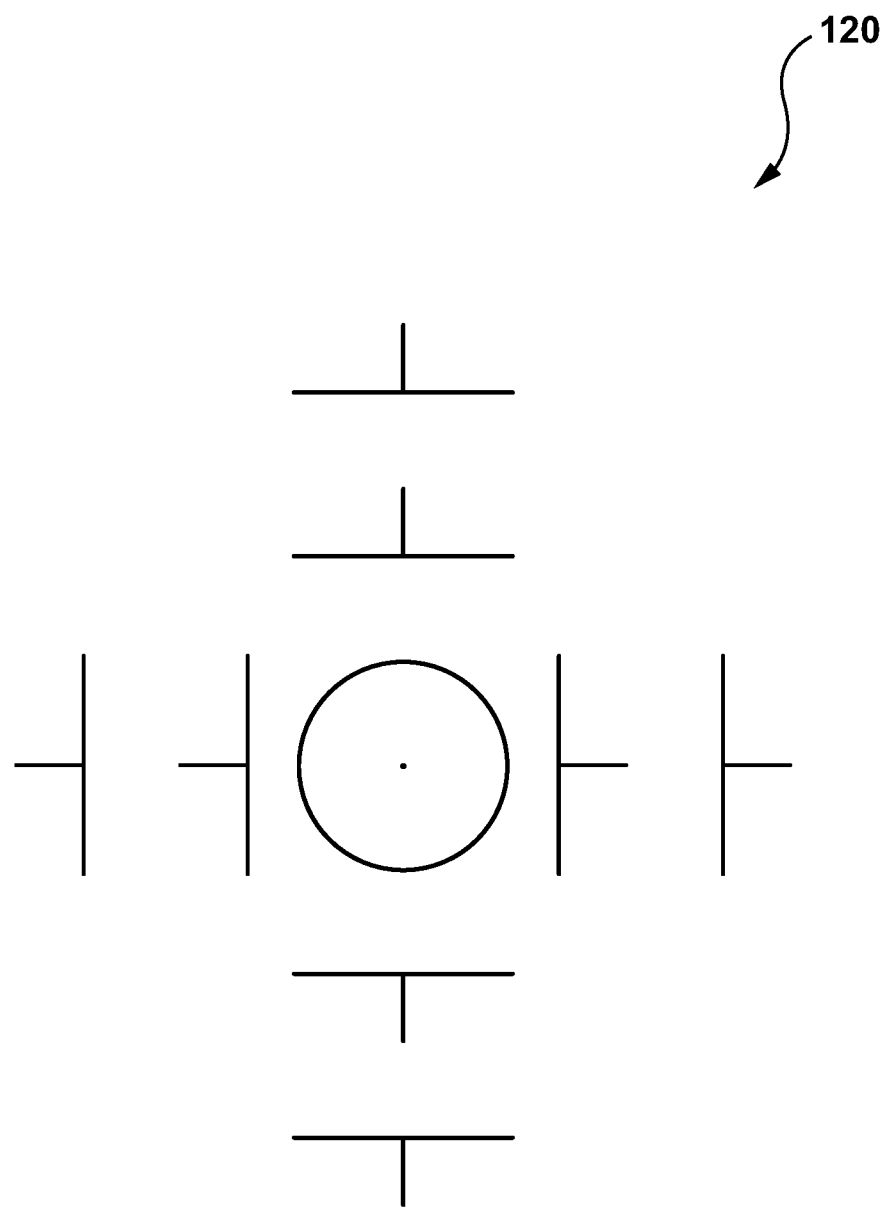
FIG. 2 is a reference pattern in accordance with another embodiment.

FIG. 2 illustrates an example of a reference pattern 120.

Reference patterns 120 are stitched into, applied (e.g. by printing), or otherwise in fixed relation with the fabric of garment 100. Reference patterns 120 may include a series of vertical, horizontal, and/or angular lines, dashes, arcs, circles, etc. with known dimensions and/or spacing therebetween when the garment is in a neutral (e.g. un-stretched) configuration. Providing known reference patterns allows an image of the reference patterns to be compared, e.g. against a known reference and/or against an image of the reference pattern taken at a different time.

Returning to FIG. 1, as deformation of garment 100 occurs (e.g. during expansion of a person's torso during a respiratory cycle), visible changes in the reference patterns—such as changes in the length, width, and/or spacing between two or more lines or points of a reference pattern—may be used to estimate a degree of expansion of the wearer's torso. For example, reference patterns in an image of the person immediately prior to inhalation may be compared with reference patterns in an image of the person immediately prior to exhalation.

For example, changes in the length and/or spacing between horizontal lines in a reference pattern may indicate expansion of the ribcage, whereas changes in the length and/or spacing of vertical lines in a reference pattern may indicate elevation and/or depression of the ribcage.

Another example of a reference pattern 120 is illustrated in FIGS. 3A-3C. With reference to FIG. 3A, illustrating a neutral configuration, reference pattern 120 includes a central vertical line 122, auxiliary vertical lines 123*a-d*, a central horizontal line horizontal line 124, auxiliary horizontal lines 125*a-d*, and a central circle 126.

FIG. 3B illustrates the reference pattern 120 of FIG. 3A in a first stretched configuration, in which garment 100 has been stretched in both a horizontal and a vertical direction at the location of the reference pattern 120. This is shown by the increase in relative spacing and curvature of auxiliary vertical lines 123*a-d* and auxiliary horizontal lines 125*a-d*, relative to the neutral configuration. Also, central circle 126 has increased in diameter relative to the neutral configuration.

FIG. 3C illustrates the reference pattern 120 of FIG. 3A in a second stretched configuration, in which garment 100 has been stretched primarily, if not exclusively, in a vertical direction at the location of the reference pattern 120. This is shown by the increase in relative spacing and curvature of auxiliary horizontal lines 125*a-d*, while auxiliary vertical lines 123*a-d* remain substantially unchanged relative to the neutral configuration. Also, central circle 126 has become elongated vertically, but not horizontally, relative to the neutral configuration.

Figure 4:
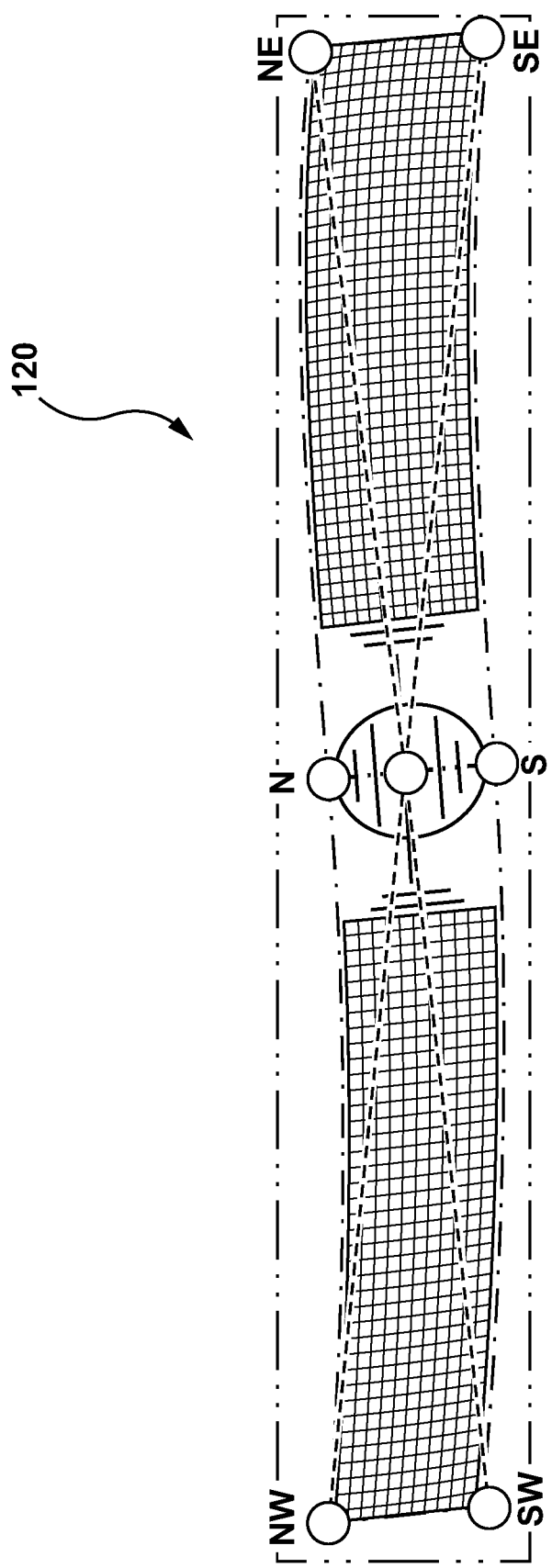
FIG. 4 is a reference pattern in accordance with another embodiment.

Another example of a reference pattern 120 is illustrated in FIG. 4. In this example, the lines and/or other markings may allow for different expansion patterns to be determined across at least two axes. Such a reference pattern may be applied, for example, on each side of the midline (e.g. at locations 120*a* and 120*b* in the example of FIG. 1) so that differential measurements for the two lungs may be taken.

Figure 5:
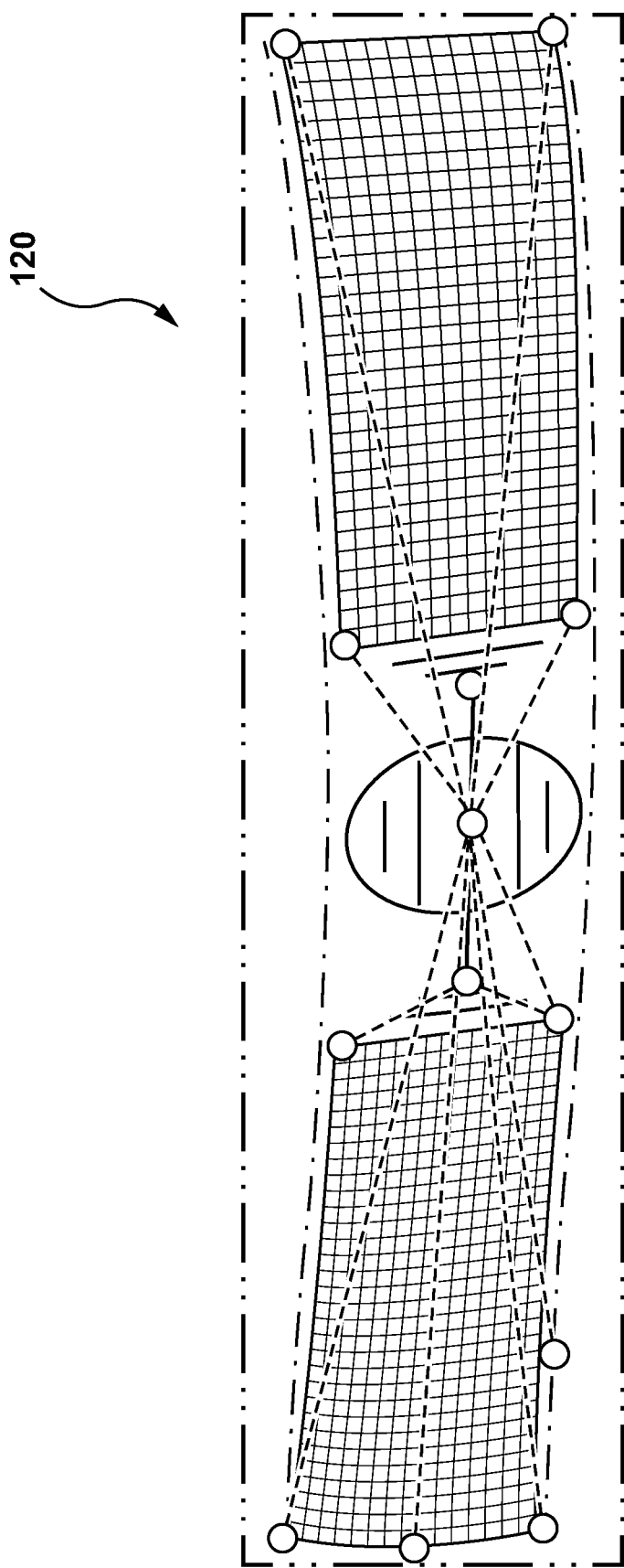
FIG. 5 is a reference pattern in accordance with another embodiment.

Another example of a reference pattern 120 is illustrated in FIG. 5. In this example, the lines and/or other markings may allow for different expansion patterns to be determined across three or more axes.

Returning to FIG. 1, additionally, or alternatively, changes in the length, width, and/or spacing between two or more reference patterns 120 may be used to estimate a degree of expansion of the wearer's torso. For example, a distance between central points of reference pattern 120*a* and 120*b* in images of the person captured immediately prior to inhalation and immediately prior to exhalation may be compared to estimate overall expansion of the torso. As another example, distances between central points of reference pattern 120*a* and/or 120*b* and a central point of reference pattern 120*c* in images of the person captured immediately prior to inhalation and immediately prior to exhalation may be compared to estimate differences in bilateral expansion of the torso.

It will be appreciated that the material and/or construction of garment 100 (e.g. a T-shirt) and its expansion co-efficient may be different for each particular garment. However, provided a person uses the same garment 100 each time images are captured, the expansion co-efficient (and other properties) of garment 100 can be expected to remain relatively constant. Accordingly, changes over time of a person's respiratory function can be monitored.

In some embodiments, two or more of reference patterns 120*a*, 120*b*, and 120*c* may be substantially identical to each other. Alternatively, each reference pattern 120 may be unique.

When a person is wearing garment 100, one or more images of the garment 100 are captured during a respiratory cycle (i.e. breathing in and breathing out). Preferably, at least one image of the person is captured immediately prior to inhalation, and at least one image of the person is captured immediately prior to exhalation.

In some embodiments, a series of images may be captured throughout a cycle of inhalation and exhalation. For example, a video clip may be recorded. Advantageously, recording a video clip may allow the person's breathing rate to be determined. For example, a person may be filmed for a fixed time period (e.g. 60 seconds), and the number of breathing cycles may be counted. Alternatively, a predetermined number of breathing cycles (e.g. one or more, or preferably 3 or 5 or more) may be captured in a video clip, and the duration of the video and the predetermined number may be used to extrapolate a breathing rate over a longer time period (e.g. 60 seconds).

Preferably, a person may capture images and/or video of themselves while wearing garment 100 and breathing normally. Alternatively, a person may have images and/or video of themselves breathing while wearing garment 100 taken by a friend, relative, caregiver, or other third party.

Preferably, images and/or video of a person wearing garment 100 are captured at different times. Images may be captured periodically on a prescribed schedule (e.g. daily, twice daily, weekly), and/or on demand, e.g. when a person is experiencing (real or perceived) breathing difficulties, such as shortness of breath.

Preferably, the person is standing or sitting upright while images of them breathing are captured.

Images captured while a person is wearing garment 100 and breathing may be sent to a remote location for storage and/or review by a technician (who may or may not be a medical professional) and/or by an automated system. The reviewer may analyze the images to determine a measure of respiratory function based on a comparison of reference patterns 120 contained in the images. For example, the reviewer may determine and/or record: a number of respirations captured in a video clip, a breathing rate, a measure of overall chest expansion during a breathing cycle, a measure of expansion of one side of the person's chest during a breathing cycle, and/or a measure of expansion of the other side of the person's chest during a breathing cycle.

When additional images are captured and sent to the remote location, the reviewer may compare measures of respiratory function based on images taken at different times in order to track changes in the person's respiratory function over time.

Optionally, one or more images captured while the person is breathing may include a visual indication of the person's body temperature. For example, a sensor (not shown) that can provide a visual indication of a temperature of the person may be included in an image. For example, a sensor may be adhered to a forehead of the person, and included in at least one captured image. Such a sensor may indicate a temperature of the person by exhibiting a distinct visual appearance (e.g. a distinct colour or pattern).

For example, in some embodiments the temperature sensor may include a strip of liquid crystals that change colour according to changes in temperature of an underlying surface. These liquid crystals may be Thermochromic Liquid Crystals (TLCs), Cholesteric Liquid Crystals, or the like. In some embodiments, the liquid crystals may be micro-encapsulated for protection, stabilization and to make the liquid crystals easier to use. For example, a FeverScan™ temperature-indicating strip (available from LCRHallcrest, Glenview, IL) may be used.

Figure 6:
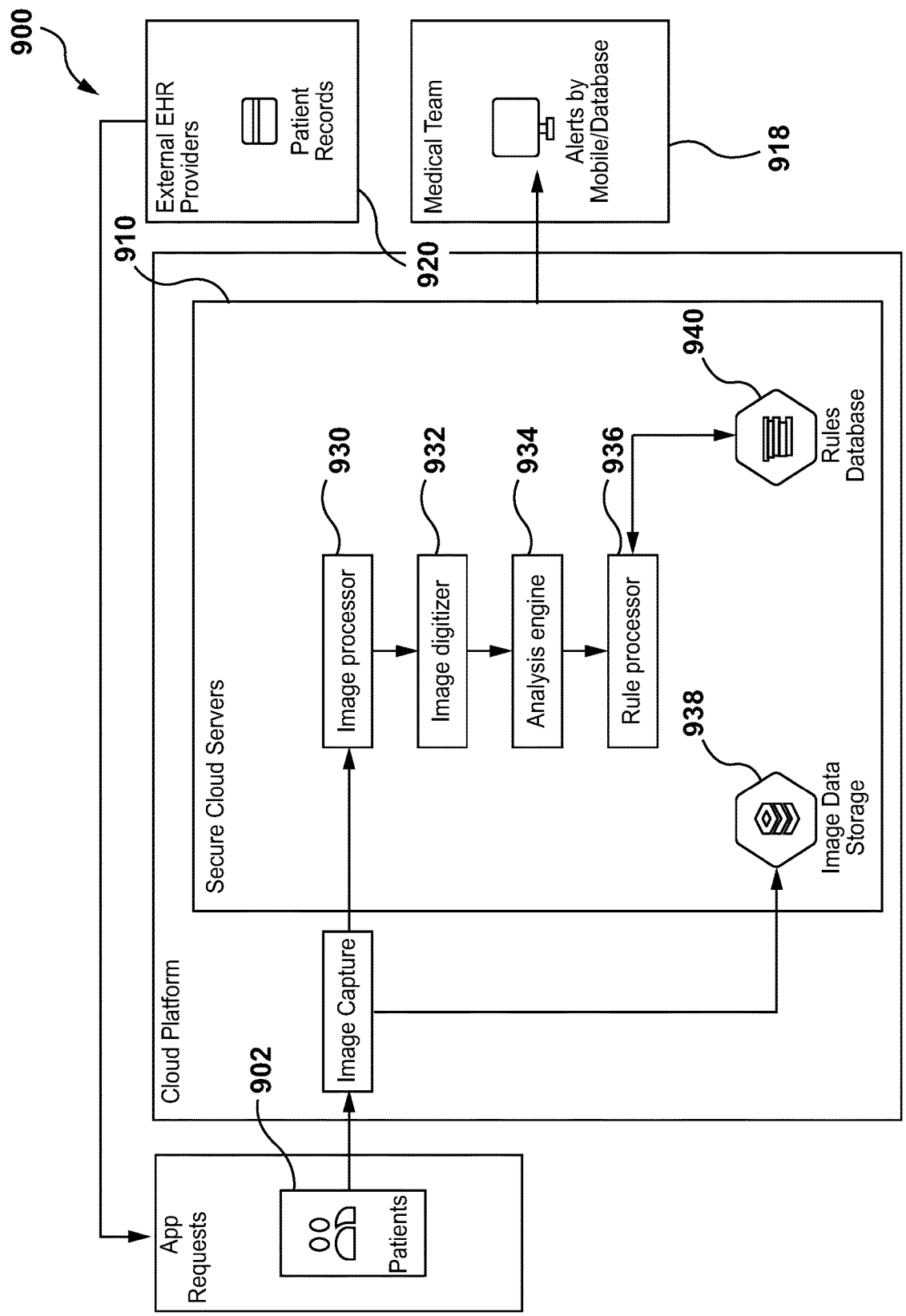
FIG. 6 is a schematic block-diagram view of a system for monitoring respiratory function, in accordance with one embodiment.

FIG. 6 schematically illustrates a system 900 for monitoring respiratory function, in accordance with one embodiment. System 900 includes at least one computing device 902 (such as a laptop, tablet, smartphone, or the like), at least one server 910 located remote from the computing device 902, and at least one computing device 918 used by a physician or other medical professional to communicate with server 910. Device 902 is used for capturing one or more images of a person who is breathing while wearing garment 100, and to transmit the one or more images (e.g. over a network, such as the Internet) to server 910. The images are received by an image processor 930 of the server 910. An image digitizer 932 may receive the images from the processor 930 and transform them into one or more sets of digital values. Once the images have been transformed to a set of digital values, they may be analyzed using an analysis engine 934 that performs and stores aggregate data analysis on the collective data. The rule processor 936 may apply various rules to the received images and/or sets of digital values to evaluate and/or compare reference patterns 120 to assess expansion of the garment 100 and therefore evaluate and/or monitor respiratory function of the person.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A system for monitoring respiratory function of a person, the system comprising:
a garment configured to be worn on a torso of the person, the garment comprising a first reference pattern positioned to overlie a first lung of the person when the garment is worn, and a second reference pattern positioned to overlie a second lung of the person when the garment is worn;
a camera configured to capture, at a first time, at least one image of the person immediately prior to inhalation, and at least one image of the person immediately prior to exhalation, and configured to capture, at a second time, at least one image of the person immediately prior to inhalation, and at least one image of the person immediately prior to exhalation; and
a computing device comprising a processor and a memory, the processor configured to execute instructions of one or more application modules, the execution of the one or more application modules causing the processor to:
establish a communication channel between the computing device and a remote computing device;
transmit, to the remote computing device, the at least one image of the person immediately prior to inhalation, and the at least one image of the person immediately prior to exhalation, captured at the first time; and
transmit, to the remote computing device, the at least one image of the person immediately prior to inhalation, and the at least one image of the person immediately prior to exhalation, captured at the second time.

2. The system of claim 1, wherein the computing device comprises the camera.

3. The system of claim 2, wherein the computing device is a mobile computing device.

4. The system of claim 3, wherein the computing device is a smartphone.

5. The system of claim 1, wherein the first reference pattern and the second reference pattern are vertically aligned with each other when the garment is worn and the torso of the person is generally upright.

6. The system of claim 1, wherein the camera is configured to capture the at least one image of the person immediately prior to inhalation, and the at least one image of the person immediately prior to exhalation, taken at the first time, as a video clip of a breathing cycle of the person.

7. The system of claim 1, wherein the execution of the one or more application modules further cause the processor to:
determine a measure of respiratory function for the person at the first time, based on a comparison of: a relative size, shape, and/or position of the first and second reference patterns in the at least one image of the person immediately prior to inhalation, captured at the first time; and a relative size, shape, and/or position of the first and second reference patterns in the at least one image of the person immediately prior to exhalation, captured at the first time.

8. The system of claim 7, wherein the execution of the one or more application modules further cause the processor to:
determine a measure of respiratory function for the person at the second time, based on a comparison of: a relative size, shape, and/or position of the first and second reference patterns in the at least one image of the person immediately prior to inhalation, captured at the second time; and a relative size, shape, and/or position of the first and second reference patterns in the at least one image of the person immediately prior to exhalation, captured at the second time.

9. The system of claim 8, wherein the execution of the one or more application modules further cause the processor to:
determine a relative measure of respiratory function for the person, based on the determined measure of respiratory function for the person at the first time and the determined measure of respiratory function for the person at the second time.

10. The system of claim 1, wherein the garment further comprises a third reference pattern positioned inferior of a sternum of the person when the garment is worn.

11. The system of claim 10, wherein the execution of the one or more application modules further cause the processor to:
determine a measure of respiratory function for the person at the first time, based on a comparison of: a relative size, shape, and/or position of at least two of the first, second, and third reference patterns in the at least one image of the person immediately prior to inhalation, captured at the first time; and a relative size, shape, and/or position of at least two of the first, second, and third reference patterns in the at least one image of the person immediately prior to exhalation, captured at the first time.

12. The system of claim 11, wherein the execution of the one or more application modules further cause the processor to:
determine a measure of respiratory function for the person at the second time, based on a comparison of: a relative size, shape, and/or position of at least two of the first, second, and third reference patterns in the at least one image of the person immediately prior to inhalation, captured at the second time; and a relative size, shape, and/or position of at least two of the first, second, and third reference patterns in the at least one image of the person immediately prior to exhalation, captured at the second time.

13. The system of claim 12, wherein the execution of the one or more application modules further cause the processor to:
determine a relative measure of respiratory function for the person, based on the determined measure of respiratory function for the person at the first time and the determined measure of respiratory function for the person at the second time.

14. The system of claim 1, further comprising:
a sensor configured to be adhered to a forehead of the person, the sensor configured to provide a visual indication of a temperature of the person;
wherein the camera is further configured to capture at least one image of the sensor when adhered to the forehead of the person; and
wherein the execution of the one or more application modules further cause the processor to:
transmit, to the remote computing device, the at least one image of the sensor.

15. A method for monitoring respiratory function of a person, the method comprising:
providing a garment configured to be worn on a torso of the person,
the garment comprising a first reference pattern positioned to overlie a first lung of the person when the garment is worn, and a second reference pattern positioned to overlie a second lung of the person when the garment is worn;
at a first time, capturing, using a camera, at least one image of the person immediately prior to inhalation, and at least one image of the person immediately prior to exhalation,
at a second time, capturing, using the camera, at least one image of the person immediately prior to inhalation, and at least one image of the person immediately prior to exhalation;
transmitting, to a remote location, the at least one image of the person immediately prior to inhalation, and the at least one image of the person immediately prior to exhalation, captured at the first time; and
transmitting, to the remote location, the at least one image of the person immediately prior to inhalation, and the at least one image of the person immediately prior to exhalation, captured at the second time.

16. The method of claim 15, wherein the capturing and the transmitting are performed using a mobile computing device comprising the camera, a processor, and a memory.

17. The method of claim 16, wherein the mobile computing device is a smartphone.

18. The method of claim 15, further comprising:
determining a measure of respiratory function for the person at the first time, based on a comparison of: a relative size, shape, and/or position of the first and second reference patterns in the at least one image of the person immediately prior to inhalation, captured at the first time; and a relative size, shape, and/or position of the first and second reference patterns in the at least one image of the person immediately prior to exhalation, captured at the first time.

19. The method of claim 18, further comprising:
determining a measure of respiratory function for the person at the second time, based on a comparison of: a relative size, shape, and/or position of at least two of the first, second, and third reference patterns in the at least one image of the person immediately prior to inhalation, captured at the second time; and a relative size, shape, and/or position of at least two of the first, second, and third reference patterns in the at least one image of the person immediately prior to exhalation, captured at the second time.

20. The method of claim 19, further comprising:
determining a relative measure of respiratory function for the person, based on the determined measure of respiratory function for the person at the first time and the determined measure of respiratory function for the person at the second time.

* * * * *